United States Patent
Tsuchiya et al.

(10) Patent No.: US 6,949,373 B2
(45) Date of Patent: Sep. 27, 2005

(54) PROTEINS HAVING A REVERSE TRANSCRIPTASE MOTIF

(75) Inventors: Masayuki Tsuchiya, Gotenba (JP); Kenji Yoshida, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 111 days.

(21) Appl. No.: 10/294,778

(22) Filed: Nov. 15, 2002

(65) Prior Publication Data

US 2003/0060417 A1 Mar. 27, 2003

Related U.S. Application Data

(62) Division of application No. 09/582,924, filed as application No. PCT/JP99/00039 on Jan. 8, 1999, now Pat. No. 6,608,188.

(30) Foreign Application Priority Data

Jan. 8, 1998 (JP) .......... 10-013232
Jan. 30, 1998 (JP) .......... 10-033584
May 6, 1998 (JP) .......... 10-139177

(51) Int. Cl.[7] .......... C12N 9/12; C07K 1/00; C07K 14/00; C07H 21/02; C07H 21/04
(52) U.S. Cl. .......... 435/194; 530/350; 536/23.2; 536/23.5
(58) Field of Search .......... 530/350; 536/23.5, 536/23.7, 23.2; 435/15, 194

(56) References Cited

FOREIGN PATENT DOCUMENTS

WO   WO 98/37181   8/1998
WO   WO 99/01560   1/1999

OTHER PUBLICATIONS

M. Meyerson et al., "hEST2, the Putative Human Telomerase Catalytic Subunit Gene, Is Up–Regulated in Tumor Cells and during Immortalization", Aug. 22, 1997, *Cell*, vol. 90, p. 785–795.
Toru Nakamura et al., "Telomerase Catalytic Subunit Homologs from Fission Yeast and Human", Aug. 15, 1997, *Science*, vol. 277, p. 955–959.
Meyerson, et al. HEST2, The Putative Human Telomerase Catalytic Subunit Gene, Is Up–Regulated in Tumor Cells and During Immortalizatgion (1997), *Cell* (90):785–795.
Nakamura, et al. Telomerase Catalytic Subunit Homologs from Fission Yeast and Human (1997) *Science* (277): 955–959.

*Primary Examiner*—Carla J. Myers
(74) *Attorney, Agent, or Firm*—Morgan, Lewis & Bockius LLP

(57) ABSTRACT

The present invention aims to provide a novel gene having a reverse transcriptase motif. The invention isolates a novel gene having a reverse transcriptase motif, and gives its complete base sequence determined. The invention also provides a protein encoded by the gene, and an antibody against the protein. The use of them is useful in developing a method for detecting telomerase activity, a method for detecting a cancer cell, a telomerase activity inhibitor, and a method for screening a telomerase activity inhibitor.

6 Claims, 1 Drawing Sheet

CORRELATION BETWEEN TELOMERASE ACTIVITY AND EXPRESSION OF CRT-1 GENE

SEQUENCE LISTING

<160> NUMBER OF SEQ ID NOS: 13

<210> SEQ ID NO 1
<211> LENGTH: 1311
<212> TYPE: DNA
<213> ORGANISM: Homo sapiens
<220> FEATURE:
<223> OTHER INFORMATION:

<400> SEQUENCE: 1

```
atg aag atg tgg aga ctc acg agg agg gcg gtc atc ttg gcc cgg       45
gtt ggc tgt gtt ccg gcc gca gag cac cgt ctg cgt gag gag atc       90
ctg gcc aag ttc ctg cac tgg ctg atg agt gtg tac gtc gtc gag      135
ctg ctc agg tct ttc ttt tat gtc acg gag acc acg ttt caa aag      180
aac agg ctc ttt ttc tac cgg aag agt gtc tgg agc aag ttg caa      225
agc att gga atc aga cag cac ttg aag agg gtg cag ctg cgg gag      270
ctg tcg gaa gca gag gtc agg cag cat cgg gaa gcc agg ccc gcc      315
ctg ctg acg tcc aga ctc cgc ttc atc ccc aag cct gac ggg ctg      360
cgg ccg att gtg aac atg gac tac gtc gtg gga gcc aga acg ttc      405
cgc aga gaa aag agg gcc gag cgt ctc acc tcg agg gtg aag gca      450
ctg ttc agc gtg ctc aac tac gag cgg gcg cgg cgc ccc ggc ctc      495
ctg ggc gcc tct gtg ctg ggc ctg gac gat atc cac agg gcc tgg      540
cgc acc ttc gtg ctg cgt gtg cgg gcc cag gac ccg ccg cct gag      585
ctg tac ttt gtc aag gtg gat gtg acg ggc gcg tac gac acc atc      630
ccc cag gac agg ctc acg gag gtc atc gcc agc atc atc aaa ccc      675
cag aac acg tac tgc gtg cgt cgg tat gcc gtg gtc cag aag gcc      720
gcc cat ggg cac gtc cgc aag gcc ttc aag agc cac gtc tct acc      765
ttg aca gac ctc cag ccg tac atg cga cag ttc gtg gct cac ctg      810
cag gag acc agc ccg ctg agg gat gcc gtc gtc atc gag cag agc      855
tcc tcc ctg aat gag gcc agc agt ggc ctc ttc gac gtc ttc cta      900
cgc ttc atg tgc cac cac gcc gtg cgc atc agg ggc aag tcc tac      945
gtc cag tgc cag ggg atc ccg cag ggc tcc atc ctc tcc acg ctg      990
ctc tgc agc ctg tgc tac ggc gac atg gag aac aag ctg ttt gcg     1035
ggg att cgg cgg gac ggg ctg ctc ctg cgt ttg gtg gat gat ttc     1080
ttg gtg aca cct cac ctc acc cac gcg aaa acc ttc ctc agg acc     1125
ctg gtc cga ggt gtc cct gag tat ggc tgc gtg gtg aac ttg cgg     1170
aag aca gtg gtg aac ttc cct gta gaa gac gag gcc ctg ggt ggc     1215
acg gct ttt gtt cag atg ccg gcc cac ggc cta ttc ccc tgg tgc     1260
ggc ctg ctg ctg gat acc cgg acc ctg gag gtg cag agc gac tac     1305
tcc agg                                                          1311
```

<210> SEQ ID NO 2
<211> LENGTH: 437
<212> TYPE: PRT
<213> ORGANISM: Homo sapiens
<220> FEATURE:
<223> OTHER INFORMATION:

<400> SEQUENCE: 2

```
Met Lys Met Trp Arg Leu Thr Arg Arg Ala Val Ile Leu Ala Arg
 1               5                  10                  15

Val Gly Cys Val Pro Ala Ala Glu His Arg Leu Arg Glu Glu Ile
                20                  25                  30

Leu Ala Lys Phe Leu His Trp Leu Met Ser Val Tyr Val Val Glu
```

-continued

```
                35                  40                  45
Leu Leu Arg Ser Phe Phe Tyr Val Thr Glu Thr Thr Phe Gln Lys
                50                  55                  60
Asn Arg Leu Phe Phe Tyr Arg Lys Ser Val Trp Ser Lys Leu Gln
                65                  70                  75
Ser Ile Gly Ile Arg Gln His Leu Lys Arg Val Gln Leu Arg Glu
                80                  85                  90
Leu Ser Glu Ala Glu Val Arg Gln His Arg Glu Ala Arg Pro Ala
                95                 100                 105
Leu Leu Thr Ser Arg Leu Arg Phe Ile Pro Lys Pro Asp Gly Leu
               110                 115                 120
Arg Pro Ile Val Asn Met Asp Tyr Val Val Gly Ala Arg Thr Phe
               125                 130                 135
Arg Arg Glu Lys Arg Ala Glu Arg Leu Thr Ser Arg Val Lys Ala
               140                 145                 150
Leu Phe Ser Val Leu Asn Tyr Glu Arg Ala Arg Arg Pro Gly Leu
               155                 160                 165
Leu Gly Ala Ser Val Leu Gly Leu Asp Asp Ile His Arg Ala Trp
               170                 175                 180
Arg Thr Phe Val Leu Arg Val Arg Ala Gln Asp Pro Pro Glu
               185                 190                 195
Leu Tyr Phe Val Lys Val Asp Val Thr Gly Ala Tyr Asp Thr Ile
               200                 205                 210
Pro Gln Asp Arg Leu Thr Glu Val Ile Ala Ser Ile Ile Lys Pro
               215                 220                 225
Gln Asn Thr Tyr Cys Val Arg Arg Tyr Ala Val Val Gln Lys Ala
               230                 235                 240
Ala His Gly His Val Arg Lys Ala Phe Lys Ser His Val Ser Thr
               245                 250                 255
Leu Thr Asp Leu Gln Pro Tyr Met Arg Gln Phe Val Ala His Leu
               260                 265                 270
Gln Glu Thr Ser Pro Leu Arg Asp Ala Val Val Ile Glu Gln Ser
               275                 280                 285
Ser Ser Leu Asn Glu Ala Ser Ser Gly Leu Phe Asp Val Phe Leu
               290                 295                 300
Arg Phe Met Cys His His Ala Val Arg Ile Arg Gly Lys Ser Tyr
               305                 310                 315
Val Gln Cys Gln Gly Ile Pro Gln Gly Ser Ile Leu Ser Thr Leu
               320                 325                 330
Leu Cys Ser Leu Cys Tyr Gly Asp Met Glu Asn Lys Leu Phe Ala
               335                 340                 345
Gly Ile Arg Arg Asp Gly Leu Leu Leu Arg Leu Val Asp Asp Phe
               350                 355                 360
Leu Val Thr Pro His Leu Thr His Ala Lys Thr Phe Leu Arg Thr
               365                 370                 375
Leu Val Arg Gly Val Pro Glu Tyr Gly Cys Val Val Asn Leu Arg
               380                 385                 390
Lys Thr Val Val Asn Phe Pro Val Glu Asp Glu Ala Leu Gly Gly
               395                 400                 405
Thr Ala Phe Val Gln Met Pro Ala His Gly Leu Phe Pro Trp Cys
               410                 415                 420
Gly Leu Leu Leu Asp Thr Arg Thr Leu Glu Val Gln Ser Asp Tyr
               425                 430                 435
```

Ser Arg

<210> SEQ ID NO 3
<211> LENGTH: 24
<212> TYPE: DNA
<213> ORGANISM: Artificial Sequence
<220> FEATURE:
<223> OTHER INFORMATION: probe

<400> SEQUENCE: 3
ccgctcgtag ttgagcacgc tgaa                                   24

<210> SEQ ID NO 4
<211> LENGTH: 19
<212> TYPE: DNA
<213> ORGANISM: Artificial Sequence
<220> FEATURE:
<223> OTHER INFORMATION: probe

<400> SEQUENCE: 4
accctcttca agtgctgtc                                         19

<210> SEQ ID NO 5
<211> LENGTH: 29
<212> TYPE: DNA
<213> ORGANISM: Artificial Sequence
<220> FEATURE:
<223> OTHER INFORMATION: probe

<400> SEQUENCE: 5
tgcgtttcct gccgagtgtg tgttgatcc                              29

<210> SEQ ID NO 6
<211> LENGTH: 30
<212> TYPE: DNA
<213> ORGANISM: Artificial Sequence
<220> FEATURE:
<223> OTHER INFORMATION: probe

<400> SEQUENCE: 6
tgcacagatg aagatgtgga gactcaggag                             30

<210> SEQ ID NO 7
<211> LENGTH: 24
<212> TYPE: DNA
<213> ORGANISM: Artificial Sequence
<220> FEATURE:
<223> OTHER INFORMATION: probe

<400> SEQUENCE: 7
agttcctgca ctggctgatg agtg                                   24

<210> SEQ ID NO 8
<211> LENGTH: 36
<212> TYPE: DNA
<213> ORGANISM: Artificial Sequence
<220> FEATURE:
<223> OTHER INFORMATION: probe

<400> SEQUENCE: 8
aagatgaagt ctcactctgt tgcccaggct ggagtg                      36

<210> SEQ ID NO 9
<211> LENGTH: 1314
<212> TYPE: DNA

<213> ORGANISM: Homo sapiens
<220> FEATURE:
<223> OTHER INFORMATION:

<400> SEQUENCE: 9

| | |
|---|---|
| atg aag atg tgg aga ctc acg agg agg gcg gtc atc ttg gcc cgg | 45 |
| gtt ggc tgt gtt ccg gcc gca gag cac cgt ctg cgt gag gag atc | 90 |
| ctg gcc aag ttc ctg cac tgg ctg atg agt gtg tac gtc gtc gag | 135 |
| ctg ctc agg tct ttc ttt tat gtc acg gag acc acg ttt caa aag | 180 |
| aac agg ctc ttt ttc tac cgg aag agt gtc tgg agc aag ttg caa | 225 |
| agc att gga atc aga cag cac ttg aag agg gtg cag ctg cgg gag | 270 |
| ctg tcg gaa gca gag gtc agg cag cat cgg gaa gcc agg ccc gcc | 315 |
| ctg ctg acg tcc aga ctc cgc ttc atc ccc aag cct gac ggg ctg | 360 |
| cgg ccg att gtg aac atg gac tac gtc gtg gga gcc aga acg ttc | 405 |
| cgc aga gaa aag agg gcc gag cgt ctc acc tcg agg gtg aag gca | 450 |
| ctg ttc agc gtg ctc aac tac gag cgg gcg cgg cgc ccc ggc ctc | 495 |
| ctg ggc gcc tct gtg ctg ggc ctg gac gat atc cac agg gcc tgg | 540 |
| cgc acc ttc gtg ctg cgt gtg cgg gcc cag gac ccg ccg cct gag | 585 |
| ctg tac ttt gtc aag gtg gat gtg acg ggc gcg tac gac acc atc | 630 |
| ccc cag gac agg ctc acg gag gtc atc gcc agc atc atc aaa ccc | 675 |
| cag aac acg tac tgc gtg cgt cgg tat gcc gtg gtc cag aag gcc | 720 |
| gcc cat ggg cac gtc cgc aag gcc ttc aag agc cac gtc tct acc | 765 |
| ttg aca gac ctc cag ccg tac atg cga cag ttc gtg gct cac ctg | 810 |
| cag gag acc agc ccg ctg agg gat gcc gtc gtc atc gag cag agc | 855 |
| tcc tcc ctg aat gag gcc agc agt ggc ctc ttc gac gtc ttc cta | 900 |
| cgc ttc atg tgc cac cac gcc gtg cgc atc agg ggc aag tcc tac | 945 |
| gtc cag tgc cag ggg atc ccg cag ggc tcc atc ctc tcc acg ctg | 990 |
| ctc tgc agc ctg tgc tac ggc gac atg gag aac aag ctg ttt gcg | 1035 |
| ggg att cgg cgg gac ggg ctg ctc ctg cgt ttg gtg gat gat ttc | 1080 |
| ttg ttg gtg aca cct cac ctc acc cac gcg aaa acc ttc ctc agg | 1125 |
| acc ctg gtc cga ggt gtc cct gag tat ggc tgc gtg gtg aac ttg | 1170 |
| cgg aag aca gtg gtg aac ttc cct gta gaa gac gag gcc ctg ggt | 1215 |
| ggc acg gct ttt gtt cag atg ccg gcc cac ggc cta ttc ccc tgg | 1260 |
| tgc ggc ctg ctg ctg gat acc cgg acc ctg gag gtg cag agc gac | 1305 |
| tac tcc agg | 1314 |

<210> SEQ ID NO 10
<211> LENGTH: 438
<212> TYPE: PRT
<213> ORGANISM: Homo sapiens
<220> FEATURE:
<223> OTHER INFORMATION:

<400> SEQUENCE: 10

Met Lys Met Trp Arg Leu Thr Arg Arg Ala Val Ile Leu Ala Arg
              5              10              15

-continued

Val Gly Cys Val Pro Ala Ala Glu His Arg Leu Arg Glu Ile
              20                  25                  30

Leu Ala Lys Phe Leu His Trp Leu Met Ser Val Tyr Val Glu
              35                  40                  45

Leu Leu Arg Ser Phe Phe Tyr Val Thr Glu Thr Thr Phe Gln Lys
              50                  55                  60

Asn Arg Leu Phe Phe Tyr Arg Lys Ser Val Trp Ser Lys Leu Gln
              65                  70                  75

Ser Ile Gly Ile Arg Gln His Leu Lys Arg Val Gln Leu Arg Glu
              80                  85                  90

Leu Ser Glu Ala Glu Val Arg Gln His Arg Glu Ala Arg Pro Ala
              95                 100                 105

Leu Leu Thr Ser Arg Leu Arg Phe Ile Pro Lys Pro Asp Gly Leu
             110                 115                 120

Arg Pro Ile Val Asn Met Asp Tyr Val Val Gly Ala Arg Thr Phe
             125                 130                 135

Arg Arg Glu Lys Arg Ala Glu Arg Leu Thr Ser Arg Val Lys Ala
             140                 145                 150

Leu Phe Ser Val Leu Asn Tyr Glu Arg Ala Arg Arg Pro Gly Leu
             155                 160                 165

Leu Gly Ala Ser Val Leu Gly Leu Asp Asp Ile His Arg Ala Trp
             170                 175                 180

Arg Thr Phe Val Leu Arg Val Arg Ala Gln Asp Pro Pro Glu
             185                 190                 195

Leu Tyr Phe Val Lys Val Asp Val Thr Gly Ala Tyr Asp Thr Ile
             200                 205                 210

Pro Gln Asp Arg Leu Thr Glu Val Ile Ala Ser Ile Ile Lys Pro
             215                 220                 225

Gln Asn Thr Tyr Cys Val Arg Arg Tyr Ala Val Val Gln Lys Ala
             230                 235                 240

Ala His Gly His Val Arg Lys Ala Phe Lys Ser His Val Ser Thr
             245                 250                 255

Leu Thr Asp Leu Gln Pro Tyr Met Arg Gln Phe Val Ala His Leu
             260                 265                 270

Gln Glu Thr Ser Pro Leu Arg Asp Ala Val Val Ile Glu Gln Ser
             275                 280                 285

Ser Ser Leu Asn Glu Ala Ser Ser Gly Leu Phe Asp Val Phe Leu
             290                 295                 300

Arg Phe Met Cys His His Ala Val Arg Ile Arg Gly Lys Ser Tyr
             305                 310                 315

Val Gln Cys Gln Gly Ile Pro Gln Gly Ser Ile Leu Ser Thr Leu
             320                 325                 330

Leu Cys Ser Leu Cys Tyr Gly Asp Met Glu Asn Lys Leu Phe Ala
             335                 340                 345

Gly Ile Arg Arg Asp Gly Leu Leu Leu Arg Leu Val Asp Asp Phe
             350                 355                 360

Leu Leu Val Thr Pro His Leu Thr His Ala Lys Thr Phe Leu Arg
             365                 370                 375

Thr Leu Val Arg Gly Val Pro Glu Tyr Gly Cys Val Val Asn Leu
             380                 385                 390

Arg Lys Thr Val Val Asn Phe Pro Val Glu Asp Glu Ala Leu Gly
             395                 400                 405

Gly Thr Ala Phe Val Gln Met Pro Ala His Gly Leu Phe Pro Trp 410                 415                 420
Cys Gly Leu Leu Leu Asp Thr Arg Thr Leu Glu Val Gln Ser Asp
                425                 430                 435

Tyr Ser Arg
        438

<210> SEQ ID NO 11
<211> LENGTH: 1866
<212> TYPE: DNA
<213> ORGANISM: Homo sapiens
<220> FEATURE:
<223> OTHER INFORMATION:

<400> SEQUENCE: 11

| | |
|---|---:|
| atg aag atg tgg aga ctc acg agg agg gcg gtc atc ttg gcc cgg | 45 |
| gtt ggc tgt gtt ccg gcc gca gag cac cgt ctg cgt gag gag atc | 90 |
| ctg gcc aag ttc ctg cac tgg ctg atg agt gtg tac gtc gtc gag | 135 |
| ctg ctc agg tct ttc ttt tat gtc acg gag acc acg ttt caa aag | 180 |
| aac agg ctc ttt ttc tac cgg aag agt gtc tgg agc aag ttg caa | 225 |
| agc att gga atc aga cag cac ttg aag agg gtg cag ctg cgg gag | 270 |
| ctg tcg gaa gca gag gtc agg cag cat cgg gaa gcc agg ccc gcc | 315 |
| ctg ctg acg tcc aga ctc cgc ttc atc ccc aag cct gac ggg ctg | 360 |
| cgg ccg att gtg aac atg gac tac gtc gtg gga gcc aga acg ttc | 405 |
| cgc aga gaa aag agg gcc gag cgt ctc acc tcg agg gtg aag gca | 450 |
| ctg ttc agc gtg ctc aac tac gag cgg gcg cgg cgc ccc ggc ctc | 495 |
| ctg ggc gcc tct gtg ctg ggc ctg gac gat atc cac agg gcc tgg | 540 |
| cgc acc ttc gtg ctg cgt gtg cgg gcc cag gac ccg ccg cct gag | 585 |
| ctg tac ttt gtc aag gtg gat gtg acg ggc gcg tac gac acc atc | 630 |
| ccc cag gac agg ctc acg gag gtc atc gcc agc atc atc aaa ccc | 675 |
| cag aac acg tac tgc gtg cgt cgg tat gcc gtg gtc cag aag gcc | 720 |
| gcc cat ggg cac gtc cgc aag gcc ttc aag agc cac gtc tct acc | 765 |
| ttg aca gac ctc cag ccg tac atg cga cag ttc gtg gct cac ctg | 810 |
| cag gag acc agc ccg ctg agg gat gcc gtc gtc atc gag cag agc | 855 |
| tcc tcc ctg aat gag gcc agc agt ggc ctc ttc gac gtc ttc cta | 900 |
| cgc ttc atg tgc cac cac gcc gtg cgc atc agg ggc aag tcc tac | 945 |
| gtc cag tgc cag ggg atc ccg cag ggc tcc atc ctc tcc acg ctg | 990 |
| ctc tgc agc ctg tgc tac ggc gac atg gag aac aag ctg ttt gcg | 1035 |
| ggg att cgg cgg gac ggg ctg ctc ctg cgt ttg gtg gat gat ttc | 1080 |
| ttg ttg gtg aca cct cac ctc acc cac gcg aaa acc ttc ctc agg | 1125 |
| acc ctg gtc cga ggt gtc cct gag tat ggc tgc gtg gtg aac ttg | 1170 |
| cgg aag aca gtg gtg aac ttc cct gta gaa gac gag gcc ctg ggt | 1215 |
| ggc acg gct ttt gtt cag atg ccg gcc cac ggc cta ttc ccc tgg | 1260 |
| tgc ggc ctg ctg ctg gat acc cgg acc ctg gag gtg cag agc gac | 1305 |
| tac tcc agc tat gcc cgg acc tcc atc aga gcc agt ctc acc ttc | 1350 |
| aac cgc ggc ttc aag gct ggg agg aac atg cgt cgc aaa ctc ttt | 1395 |

-continued

```
ggg gtc ttg cgg ctg aag tgt cac agc ctg ttt ctg gat ttg cag        1440
gtg aac agc ctc cag acg gtg tgc acc aac atc tac aag atc ctc        1485
ctg ctg cag gcg tac agg ttt cac gca tgt gtg ctg cag ctc cca        1530
ttt cat cag caa gtt tgg aag aac ccc aca ttt ttc ctg cgc gtc        1575
atc tct gac acg gcc tcc ctc tgc tac tcc atc ctg aaa gcc aag        1620
aac gca ggg atg tcg ctg ggg gcc aag ggc gcc gcc ggc cct ctg        1665
ccc tcc gag gcc gtg cag tgg ctg tgc cac caa gca ttc ctg ctc        1710
aag ctg act cga cac cgt gtc acc tac gtg cca ctc ctg ggg tca        1755
ctc agg aca gcc cag acg cag ctg agt cgg aag ctc ccg ggg acg        1800
acg ctg act gcc ctg gag gcc gca gcc aac ccg gca ctg ccc tca        1845
gac ttc aag acc atc ctg gac                                        1866
```

<210> SEQ ID NO 12
<211> LENGTH: 622
<212> TYPE: PRT
<213> ORGANISM: Homo sapiens
<220> FEATURE:
<223> OTHER INFORMATION:

<400> SEQUENCE: 12

```
Met Lys Met Trp Arg Leu Thr Arg Arg Ala Val Ile Leu Ala Arg
              5                  10                  15

Val Gly Cys Val Pro Ala Ala Glu His Arg Leu Arg Glu Glu Ile
             20                  25                  30

Leu Ala Lys Phe Leu His Trp Leu Met Ser Val Tyr Val Val Glu
             35                  40                  45

Leu Leu Arg Ser Phe Phe Tyr Val Thr Glu Thr Thr Phe Gln Lys
             50                  55                  60

Asn Arg Leu Phe Phe Tyr Arg Lys Ser Val Trp Ser Lys Leu Gln
             65                  70                  75

Ser Ile Gly Ile Arg Gln His Leu Lys Arg Val Gln Leu Arg Glu
             80                  85                  90

Leu Ser Glu Ala Glu Val Arg Gln His Arg Glu Ala Arg Pro Ala
             95                 100                 105

Leu Leu Thr Ser Arg Leu Arg Phe Ile Pro Lys Pro Asp Gly Leu
            110                 115                 120

Arg Pro Ile Val Asn Met Asp Tyr Val Val Gly Ala Arg Thr Phe
            125                 130                 135

Arg Arg Glu Lys Arg Ala Glu Arg Leu Thr Ser Arg Val Lys Ala
            140                 145                 150

Leu Phe Ser Val Leu Asn Tyr Glu Arg Ala Arg Arg Pro Gly Leu
            155                 160                 165

Leu Gly Ala Ser Val Leu Gly Leu Asp Asp Ile His Arg Ala Trp
            170                 175                 180

Arg Thr Phe Val Leu Arg Val Arg Ala Gln Asp Pro Pro Glu
            185                 190                 195

Leu Tyr Phe Val Lys Val Asp Val Thr Gly Ala Tyr Asp Thr Ile
            200                 205                 210

Pro Gln Asp Arg Leu Thr Glu Val Ile Ala Ser Ile Ile Lys Pro
            215                 220                 225

Gln Asn Thr Tyr Cys Val Arg Arg Tyr Ala Val Val Gln Lys Ala
```

-continued

```
                230                 235                 240
Ala His Gly His Val Arg Lys Ala Phe Lys Ser His Val Ser Thr
                245                 250                 255
Leu Thr Asp Leu Gln Pro Tyr Met Arg Gln Phe Val Ala His Leu
                260                 265                 270
Gln Glu Thr Ser Pro Leu Arg Asp Ala Val Ile Glu Gln Ser
                275                 280                 285
Ser Ser Leu Asn Glu Ala Ser Ser Gly Leu Phe Asp Val Phe Leu
                290                 295                 300
Arg Phe Met Cys His His Ala Val Arg Ile Arg Gly Lys Ser Tyr
                305                 310                 315
Val Gln Cys Gln Gly Ile Pro Gln Gly Ser Ile Leu Ser Thr Leu
                320                 325                 330
Leu Cys Ser Leu Cys Tyr Gly Asp Met Glu Asn Lys Leu Phe Ala
                335                 340                 345
Gly Ile Arg Arg Asp Gly Leu Leu Leu Arg Leu Val Asp Asp Phe
                350                 355                 360
Leu Leu Val Thr Pro His Leu Thr His Ala Lys Thr Phe Leu Arg
                365                 370                 375
Thr Leu Val Arg Gly Val Pro Glu Tyr Gly Cys Val Val Asn Leu
                380                 385                 390
Arg Lys Thr Val Val Asn Phe Pro Val Glu Asp Glu Ala Leu Gly
                395                 400                 405
Gly Thr Ala Phe Val Gln Met Pro Ala His Gly Leu Phe Pro Trp
                410                 415                 420
Cys Gly Leu Leu Leu Asp Thr Arg Thr Leu Glu Val Gln Ser Asp
                425                 430                 435
Tyr Ser Ser Tyr Ala Arg Thr Ser Ile Arg Ala Ser Leu Thr Phe
                440                 445                 450
Asn Arg Gly Phe Lys Ala Gly Arg Asn Met Arg Arg Lys Leu Phe
                455                 460                 465
Gly Val Leu Arg Leu Lys Cys His Ser Leu Phe Leu Asp Leu Gln
                470                 475                 480
Val Asn Ser Leu Gln Thr Val Cys Thr Asn Ile Tyr Lys Ile Leu
                485                 490                 495
Leu Leu Gln Ala Tyr Arg Phe His Ala Cys Val Leu Gln Leu Pro
                500                 505                 510
Phe His Gln Gln Val Trp Lys Asn Pro Thr Phe Phe Leu Arg Val
                515                 520                 525
Ile Ser Asp Thr Ala Ser Leu Cys Tyr Ser Ile Leu Lys Ala Lys
                530                 535                 540
Asn Ala Gly Met Ser Leu Gly Ala Lys Gly Ala Ala Gly Pro Leu
                545                 550                 555
Pro Ser Glu Ala Val Gln Trp Leu Cys His Gln Ala Phe Leu Leu
                560                 565                 570
Lys Leu Thr Arg His Arg Val Thr Tyr Val Pro Leu Leu Gly Ser
                575                 580                 585
Leu Arg Thr Ala Gln Thr Gln Leu Ser Arg Lys Leu Pro Gly Thr
                590                 595                 600
Thr Leu Thr Ala Leu Glu Ala Ala Asn Pro Ala Leu Pro Ser
                605                 610                 615
Asp Phe Lys Thr Ile Leu Asp
                620     622
```

```
<210> SEQ ID NO 13
<211> LENGTH: 37
<212> TYPE: DNA
<213> ORGANISM: Artificial Sequence
<220> FEATURE:
<223> OTHER INFORMATION: probe

<400> SEQUENCE: 13
ctgaaaaact catatattca gtattttact cccacag                              37
```

PROTEINS HAVING A REVERSE TRANSCRIPTASE MOTIF

This is a divisional of application Ser. No. 09/582,924, filed on Jul. 7, 2000 now U.S. Pat. No. 6,608,188, which is a national stage application of PCT/JP99/00039, filed Jan. 8, 1999.

TECHNICAL FIELD

This invention relates to a novel gene having a reverse transcriptase motif, a protein encoded by the gene, an antibody against the protein, and a method for detecting reverse transcriptase activity, a method for detecting a cancer cell, and a reverse transcriptase activity inhibitor or a method for screening a reverse transcriptase activity inhibitor, each of the methods and the inhibitor using any of the novel gene, the protein, and the antibody.

The invention also relates to a method for diagnosing cancer by the use of the above detecting method, a cancer diagnostic agent containing a probe complementary to the gene, and a cancer diagnostic agent containing the antibody.

BACKGROUND ART

Telomerase is an enzyme known to have the function of repairing the length of telomere which is shortened by each cell division (Greider C. W. and Blackburn E. H., (1987) Cell, 51, 887–898; Morin G. B. (1989) Cell, 59, 521–529).

Most cancer cells show telomerase activity (Kim N. W. et al., (1994) Science, 206, 2011–2015), a finding strongly suggesting that telomerase takes part in maintaining the infinite proliferation of cancer cells.

The measurement of telomerase activity, therefore, is important for diagnosis of cancer, and a substance inhibiting telomerase activity can be expected to serve as an anticancer drug causing few adverse reactions to normal cells (Counter C. M. et al., (1989) EMBO J., 11, 1921–1929; Counter C. M. et al., (1994) Proc. Natl. Acad. Sci. USA, 91, 2900–2904; Chadenneau C. et al., (1995) Cancer Res., 55, 2533–2536; Hiyama E. et al., (~1995) Nature Med., 1, 249–255; Shay J. W. et al., (1995) Mol. Cell. Biol., 15, 425–432).

One of conventional methods for measuring telomerase activity is to measure telomerase enzyme activity.

According to this method, a cell extract needs to be prepared beforehand, with enzyme activity being maintained. Then, a telomere elongation reaction (telomerase reaction) is performed. The elongated telomere is measured for the amount of the resulting DNA, directly or after amplification by polymerase chain reaction (PCR). This method was not a convenient, effective method for measuring telomerase activity.

Another method for measuring telomerase activity is to measure the expression of a telomerase gene. Such a method requires the identification of the gene correlated to telomerase activity.

As one of such genes, a gene encoding a protein having a reverse transcriptase motif with a molecular weight of about 130 kDa was recently isolated from mRNA derived from a human testis or a cancer cell (Meyerson M., et al., (1997) Cell, 90, 785–795; Nakamura T. M. et al., (1997) Science, 277, 955–959).

Since the expression of this gene showed high correlation with telomerase activity, this gene has been speculated to code for a human telomerase catalytic subunit.

However, much is yet unknown about telomerase.

For example, it is still unknown whether a plurality of genes having a reverse transcriptase motif exists, and whether a gene, or a plurality of genes, showing telomerase activity exist. It is also unknown whether the telomerase activity of a normal germ cell and that of a cancer cell always come from the same genetic product, and whether the telomerase activities of all cancer cells can be explained by a single gene. Solutions to these questions are desperately wanted in the fields of cancer diagnosis and treatment focusing on telomerase.

DISCLOSURE OF THE INVENTION

The present invention aims to provide a novel gene encoding a protein having a reverse transcriptase motif, the novel gene having correlation with reverse transcriptase activity.

The invention also aims to provide a protein encoded by the gene, and an antibody against the protein.

The invention further aims to provide a method for measuring reverse transcriptase activity, and a method for detecting a cancer cell, each method using the gene, the protein, or the antibody.

The reverse transcriptase as used herein refers collectively to nucleic acid polymerases which perform DNA synthesis using RNA as template. A known representative reverse transcriptase is that found in retroviruses.

Telomerase synthesizes a telomere DNA sequence by using its own subunit, single-stranded RNA, as template. Thus, telomerase is positioned as an associate of RNA-dependent DNA polymerases, i.e., an associate of reverse transcriptases.

In the present specification, reverse transcriptase activity refers, preferably, to telomerase enzyme activity.

BRIEF DESCRIPTION OF THE DRAWINGS

In FIG. 1, PC93, COLO203, HCT-15, DU145, LNCap, PC3, MCF7, SC6, HL60, and WI-38 denote, respectively, cell strains from prostatic cancer, colon cancer, colon cancer, prostatic cancer, prostatic cancer, prostatic cancer, mammary carcinoma, gastric cancer, promyelocytic leukemia, and a cell strain derived from the lung. Testis denotes a testis (tissue).

BEST MODE FOR CARRYING OUT THE INVENTION

Figure 1:
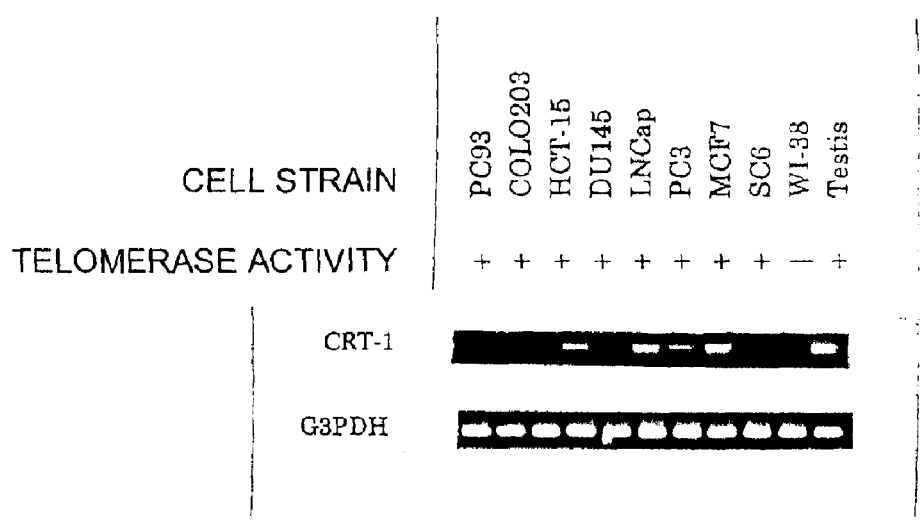
FIG. 1 is electrophoretic pattern photographs showing the correlation between telomerase activity and the expression of CRT-1 gene.

In the light of the aforementioned questions, the inventors of the present invention conducted extensive studies in an attempt to discover a novel gene having correlation with reverse transcriptase activity. As a result, the inventor found out a novel gene encoding a protein having a reverse transcriptase motif from a human promyelocytic leukemia cell strain HL60 cell, and confirmed correlation between the expression of the resulting gene and reverse transcriptase activity. These findings have led the inventor to accomplish this invention.

Therefore, the use of the gene according to the invention, a protein encoded by the gene, or an antibody against the protein makes it possible to measure reverse transcriptase activity, and to control the expression of reverse transcriptase activity.

Furthermore, it becomes possible to design an inhibitor of the activity, or to develop a method for screening an inhibitor of reverse transcriptase activity.

More particularly, the invention provides a gene, a protein, an antibody, a method for detecting a cancer cell, a reverse transcriptase activity inhibitor, a method for screening the inhibitor, a reverse transcriptase activity regulator, a ribozyme, a reverse transcriptase activity suppressor, a method for screening a reverse transcriptase activity inducer, and a reverse transcriptase activity inducer, as described below.

1. A CRT-1 gene comprising a base sequence set forth in SEQ ID NO: 1, 9 or 11 in the Sequence Listing.

2. A gene encoding a protein comprising an amino acid sequence set forth in SEQ ID NO: 2, 10 or 12 in the Sequence Listing.

3. A gene encoding a protein comprising an amino acid sequence obtained by substituting or deleting one or more amino acids of an amino acid sequence set forth in SEQ ID NO: 2, 10 or 12 in the Sequence Listing, or by adding one or more amino acids to an amino acid sequence set forth in SEQ ID NO: 2, 10 or 12 in the Sequence Listing, wherein the protein has reverse transcriptase activity.

4. A gene which is hybridized under stringent conditions with the gene according to any one of 1 to 3 above, and which encodes a protein having reverse transcriptase activity.

5. A protein comprising an amino acid sequence set forth in SEQ ID NO: 2, 10 or 12 in the Sequence Listing.

6. A protein comprising an amino acid sequence obtained by substituting or deleting one or more amino acids of an amino acid sequence set forth in SEQ ID NO: 2, 10 or 12 in the Sequence Listing, or by adding one or more amino acids to an amino acid sequence set forth in SEQ ID NO: 2, 10 or 12 in the Sequence Listing, the protein having reverse transcriptase activity.

7. An antibody against the protein according to any one of 5 and 6 above.

8. An oligonucleotide comprising a base sequence of an antisense strand of the gene according to any one of 1 to 4 above.

9. A method for detecting a cancer cell, comprising detecting the gene according to any of 1 to 4 above.

10. A method for detecting a cancer cell, comprising using the antibody against the protein according to 7 above.

11. A reverse transcriptase activity inhibitor having an oligonucleotide comprising the base sequence according to any one of 1 to 4 above.

12. A method for screening a reverse transcriptase activity inhibitor, comprising using an oligonucleotide comprising the base sequence according to any one of 1 to 4 above.

13. A method for detecting a cancer cell, comprising detecting the gene according to any one of 1 to 4 above.

14. A reverse transcriptase activity inhibitor having an oligonucleotide comprising the base sequence according to any one of 1 to 4 above.

15. A method for screening a reverse transcriptase activity inhibitor, comprising using an oligonucleotide comprising the base sequence according to any one of 1 to 4 above.

16. An agent which acts on the CRT-1 gene to regulate reverse transcriptase activity.

17. A ribozyme of the CRT-1 gene.

18. An intracellular antibody against the CRT-1 protein.

19. A reverse transcriptase activity suppressor comprising a dominant negative protein of the CRT-1 protein.

20. A method for screening a reverse transcriptase activity inducer, comprising using the CRT-1 protein or gene.

21. A reverse transcriptase activity derivative comprising the CRT-1 gene, the CRT-1 protein, or a mutant thereof.

22. A method for diagnosing cancer, comprising using the above method for detecting a cancer cell.

23. A cancer diagnostic agent comprising a probe complementary to the gene above.

24. A cancer diagnostic agent comprising the antibody above.

The present invention will now be described in more detail by reference to its embodiments.

If a gene refers definitely to DNA obtained by reverse transcription from mRNA present in nature (DNA obtained by amplification of the DNA is included), the gene is called cDNA.

(Gene Having a Reverse Transcriptase Motif)

A gene having a reverse transcriptase motif according to the present invention can be obtained by the following procedure:

(1) Prepare mRNA from a human-derived cell.

Concretely, HL-60 can be used preferably.

(2) Prepare total RNA from the selected cell.

In constituting such total RNA, a publicly known method can be used preferably.

(3) Then, prepare poly(A)+RNA(mRNA).

There are no restrictions on a method for preparing it, and a publicly known method or a commercially available kit can be used.

(4) Based on the resulting mRNA, construct a cDNA library of HL-60 for use in 5'RACE and 3'RACE.

There are no restrictions on a method for preparing it, and a publicly known method or a commercially available kit can be used.

(5) No restriction is imposed in selecting primers for use in the 5'RACE method. However, primers for amplifying the 5' region of a gene having a reverse transcriptase-like motif can be designed based, for example, on a human-derived EST clone (GenBank Accession Number AA281296) having high homology to a telomerase catalytic subunit of Ciliophora Euplotes or the yeast *S. cerevisiae*.

Concretely, primers used in Examples to be offered later on can be quoted.

Synthesis of primers can be achieved with the desired purity by an ordinary method.

(6) There are no restrictions on the conditions for amplification of gene, but optimal conditions for amplification can be selected by publicly known methods.

A commercially available kit can also be used.

Concretely, the conditions for amplification are those used in the Examples.

(7) After purifying the resulting reaction product, subclone it into a suitable vector, and determine the base sequences of gene fragments cloned.

There are no restrictions on the usable subcloning vector, but concretely, the vector used in the Examples is preferred.

A commercially available kit can also be used.

There are no restrictions on a method for base sequencing, and a publicly known method, and a sequencer using it, can be used (e.g., Taq cycle sequencing, the method described in "Biotechniques, vol. 7", (1989), pp. 494–499). (8) The primers for the 3'RACE method can also be designed in the same manner as the primer designing for 5'RACE.

Concretely, the sequences used in the Examples are cited.

As for the conditions for amplification, optimal conditions can be selected as with the 5'RACE method.

Concretely, the conditions used in the Examples can be cited.

A commercially available kit can also be used.

(9) Similarly purify the resulting reaction product, subclone it into a suitable vector, and determine the base sequences of the resulting clones.

(10) A gene of the total length can be yielded by designing primers, which are hybridized with the 5'-terminal and 3'-terminal of cDNA, from the gene fragments obtained by the 5'RACE and 3'RACE methods described above, and performing a suitable amplification reaction.

As such an amplification reaction, RT-PCR used in the Example can be used preferably.

There are no restrictions on a method for determining the base sequence of the resulting gene, and a publicly known method, and a sequencer using it, can be used.

(Detection of Tissue Distribution, Method for Detecting Cancer Cell, Method for Screening Anticancer Drug)

It is possible to prepare a probe with the use of a fragment of the resulting gene, and find out a tissue in which the gene is expressed.

For example, the probe can be labeled with a publicly known means of labeling, and a publicly known northern blotting method can be performed.

Also, the gene expressed in a particular tissue can be assayed by use of a particular standard material.

Thus, telomerase activity can be confirmed by detecting the expression of the gene.

If telomerase activity is related to the presence of a cancer cell, detection and assay of such gene provide a method for detecting a cancer cell.

Similarly, quantitative determination of the expression of the gene provides a method for ascertaining the effect of an anticancer drug.

In this case, the effect of the anticancer drug can be confirmed by investigating changes in the amount of gene expression depending on whether the anticancer drug was administered or not, or changes in the amount of the gene expressed within a particular period of time after administration of the anticancer drug.

(Protein, Method for Detecting Cancer Cell)

The above-described method makes it possible to obtain a human-derived novel gene having a reverse transcriptase motif according to the invention, and identify the amino acid sequence of a protein encoded by the gene from information on the base sequence of the gene.

That is, the protein encoded by the novel gene of the invention is a protein comprising the amino acid sequence set forth in SEQ ID NO: 3 in the Sequence Listing.

Furthermore, the protein of the invention is not restricted to this amino acid sequence, and includes a protein obtained by substituting or deleting one or more amino acids of the amino acid sequence, or by adding one or more amino acids to the amino acid sequence, the protein having telomerase activity (i.e., a mutant protein).

Hence, examples of a polynucleotide encoding the protein having telomerase activity of the invention include not only a polynucleotide comprising the base sequence set forth in SEQ ID NO: 1 in the Sequence Listing, but also the same polynucleotide whose structure has been partly changed by spontaneous or artificial mutation without changing telomerase activity, the main function of a polypeptide encoded by the polynucleotide (i.e., a mutant gene).

Regarding methods for introducing such an artificial mutation, reference should be made, for example, to "Molecular Cloning 2nd Edition" (Cold Spring Harbor Laboratory Press, 1989) pp. 15.1–15.113.

Also, a gene to be obtained by replacing at least some bases of the base sequence of the gene by other types of bases as a result of degeneracy of the genetic codes can give a protein having the same amino acid sequence.

Therefore, the gene encoding the protein of the invention includes all degeneracy patterns capable of encoding the protein of the invention and mutant proteins derived from the protein.

There are no restrictions on a method for obtaining the protein of the invention (including mutant proteins).

Examples of the method are various methods, such as a method of artificial peptide synthesis by a protein synthesizer or the like, and methods for expressing proteins by genetic engineering on the basis of information on the base sequence of the gene encoding the protein obtained by the invention.

The CRT-1 protein may be expressed alone or as a fusion protein fused to MBP (maltose binding protein) or the like, or may be expressed in a form having a tag, such as FLAG peptide, added thereto.

The genetic engineering technique enables the protein to be prepared by use of bacteria, such as E. coli, or yeast, or animal cells or insect cells.

An example is a method for obtaining a transformant by selecting a suitable vector and a suitable host, and introducing the gene (for example, this can be achieved by the method described in "Cell Engineering Protocol", Shujun-Sha, 1991, pp. 105–107).

The resulting transformant is cultured to amplify the gene and express a protein, whereby the desired protein can be expressed.

Then, the cultures are collected, and if desired, concentrated, solubilized, dialyzed, and variously chromatographed, whereby the protein of the invention and mutant proteins therefrom can be obtained.

For the culturing of the transformant, various textbooks are available. For instance, the method described in "Methods of Microbial Experiments" (the Japanese Biochemical Society, Tokyo Kagaku Dojin, 1992) can be employed.

The expression of the desired protein (including mutant proteins) based on the base sequence described in the invention can be carried out by a publicly known method.

For this purpose, the host may be any of bacteria such as E. coli, yeast, and animal cells. Particularly, animal cells are preferred.

To incorporate the gene into a cell, the liposome method, the electroporation method, etc. can be used.

The use of the DEAE-dextran method (Pharmacia), in particular, is preferred.

Purification methods for purifying a protein from the resulting culture include immunoprecipitation, salting-out, ultrafiltration, isoelectric precipitation, gel filtration, electrophoresis, ion exchange chromatography, various affinity chromatographic techniques such as hydrophobic chromatography and antibody chromatography, chromatofocusing, adsorption chromatography, and reverse phase chromatography. Any of these methods may be selected suitably.

In the manufacturing stage, the desired protein may be produced by a transformant as a fusion peptide fused to other polypeptide.

If desired, the fusion product may be treated with a chemical substance, such as cyanogen bromide, or an enzyme, such as protease, in the purification step to cut out the desired protein.

(Antibody, Method for Detecting Cancer Cell by Use of Antibody)

A method for obtaining an antibody against all of or a part of the resulting protein (including mutant proteins) may be a publicly known method.

The antibody of the invention includes a polyclonal antibody and a monoclonal antibody, as long as each of the antibodies reacts with the protein of the invention (or its mutant).

Its active fragment, and a chimeric antibody containing the active fragment are also included.

An antibody, i.e., an immunoglobulin, has an H chain and an L chain, and is classified into five classes (IgA, IgD, IgE, IgG, IgM) by physicochemical properties and immunological properties.

Of these classes, IgA and IgG are further divided into subclasses by the type of the H chain.

The novel antibody of the invention includes those belonging to all these classes and subclasses.

Furthermore, the antibody of the invention does not necessarily need to be the entire antibody molecule, but may be a part of the molecule (active fragment), if it has activity.

Examples of the active fragment are F(ab')$_2$, Fab', Fab, Fv, recombinant Fv, and single-stranded Fv.

For example, decomposition with pepsin gives F(ab')$_2$ and Fc', while decomposition with papain gives Fab and Fc.

These active fragments may be used alone, but if desired, may be used as a new complex formed by their joining to substances such as albumin or polyethylene glycol.

Generally, such a complex shows its effect to maximum in vivo without being decomposed for a long time.

Methods for performing the addition of a substance, such as albumin or polyethylene glycol, to an active fragment are described, for example, in "Antibodies, A Laboratory Manual" (Cold Spring Herber Laboratory, 1988), pp. 77–81 and pp. 129–137.

Generally, the active fragment can be easily bound to albumin or the like by using a bifunctional reagent, such as SPDP (Pharmacia), SMPB (Pias) or EMCS (Dotite).

For a method for preparing the antibody of the invention, reference can be made, for example, to "Method for Handling Immunological Experiments" (edited and published by The Japanese Society for Immunology).

An immunogen may be a part of the protein of the invention, i.e., the amino acid sequence set forth in SEQ ID NO: 2 in the Sequence Listing, or a polypeptide comprising 8 or more consecutive amino acids of the amino acid sequence of the mutant protein.

If the protein as the immunogen has been purified to such a degree that it can be used for the preparation of an antibody, the protein may be obtained by whatever method.

If the immunogen is a polypeptide comprising 8 to about 20 amino acids, it may be bound to a carrier such as keyhole-limpet hemocyanin (KLH) for use as an antigen.

An animal to be immunized with the immunogen may be any animal other than human, and it is preferred to select an animal species, capable of producing the desired antibody, from animals usually used among people skilled in the art.

The polyclonal antibody is obtained by purifying the resulting antiserum.

Purification may be performed by combining methods, such as salting-out, ion exchange chromatography, and affinity chromatography.

The monoclonal antibody is obtained by obtaining a fused cell by an ordinary method for preparing a hybridoma, and then causing the fused cell to produce an antibody.

For cell fusion, a technique using polyethylene glycol, Sendai virus, or electric pulses is usable.

In addition to the above methods, a genetic engineering method may be used to obtain the monoclonal antibody.

For example, mRNA is collected from splenic cells or lymphocytes of an animal immunized with the protein of the invention or a part of the protein, or from a hybridoma which produces the monoclonal antibody, and a cDNA library is constructed based on the mRNA.

Then, antibodies are expressed from the cDNA library.

Clones producing the antibodies reactive with the antigen are obtained from the cDNA library by screening. The resulting clones are cultured, and the desired antibody can be purified from the culture mixture by a combination of methods, such as salting-out, ion exchange chromatography, and affinity chromatography.

The resulting antibody of the invention can be used to detect telomerase which is present in various tissues.

In detecting it, western blotting, a usually employed method, can be used preferably.

The antibody can be used in preparing an antibody column, which is used for purifying the protein of the invention, its mutant, or a part of the protein or the mutant. The antibody is also usable in detecting the protein, its mutant, or a part of the protein or the mutant which is contained in respective fractions.

Furthermore, the use of a particular standard material makes it possible to assay telomerase expressed in a particular tissue.

Thus, telomerase activity can be confirmed by detecting the expression of the telomerase.

If telomerase activity is related to the existence of a cancer cell, detection and assay of such telomerase provide a method for detecting a cancer cell.

Similarly, quantitative analysis of the expression of the telomerase provides a method for ascertaining the effect of an anticancer drug.

In this case, the effect of the anticancer drug can be confirmed by investigating changes in the amount of telomerase expression depending on whether the anticancer drug was administered or not, or changes in the amount of telomerase expression within a particular period of time after administration of the anticancer drug.

As another clinical application, diagnosis of cancer can be made, for example, by taking an extract of a cell or a pathological tissue as a specimen, and examining the presence or absence of the gene of the invention therein.

Concretely, there is a method which uses a sequence complementary to the gene as a probe to examine the presence or absence of the gene.

The length of the sequence used as the probe is 10 to 1,300 bases, preferably 10 to 1,000 bases, more preferably 20 to 400 bases.

In examining the presence or absence of the gene, the gene may be or need not be amplified. As a means of amplification, RT-PCR, or TMA (transcription mediated amplification, Japanese Laid-Open Patent Application, Hei 4-500759) can be used.

As a means of detection, HPA (hybridization protection assay, Japanese Laid-Open Patent Application, Hei 2-5043147) can be used.

As a concrete method for diagnosis of cancer, the method described, for example, in Japanese Laid-Open Patent Application, Hei9-502102or U.S. Pat. No. 5,489,508 can be used.

Particularly if the material used is a pathological tissue, in situ hybridization using the aforementioned probe, for example, is usable.

It is also possible to use ABC tissue staining which uses the antibody of the invention.

(Antisense Oligonucleotide, Telomerase Activity Inhibitor, Method for Screening Telomerase Activity Inhibitor)

An antisense polynucleotide based on the above-mentioned gene obtained by the invention includes all of a plurality of nucleotides bound together, which comprise bases, phosphates and sugars, and those which are naturally nonexistent.

Typical of them are DNA and mRNA.

The antisense polynucleotide derivatives of the invention include those which are similar to polynucleotides in stereostructure and function.

Examples are those in which other substances have been bound to the 3'-terminal or 5'-terminal of polynucleotides, polynucleotides in which a modification, such as substitution, deletion or addition, has occurred in at least some of the bases, sugars or phosphates, those having bases, sugars or phosphates which are not naturally existent, and those having a skeleton other than a sugar-phosphate skeleton.

The antisense polynucleotide and its derivatives may be those which can be hybridized with the gene of the invention and any portions of its mutant gene.

The antisense polynucleotide and its derivatives can be used as a research polynucleotide probe for investigating the existence or expression status of the gene encoding the protein or its mutant of the invention contained in a tissue or cell.

They are also usable as polynucleotide probes for diagnosis.

As probes, those which have 12 or more bases and a GC content of 30 to 70% are preferred, and those which have 16 or more bases and a GC content of 30 to 70% are particularly preferred.

By using the antisense polynucleotide and its derivatives, the expression of the protein (including its mutant) of the invention can be regulated.

This is because they can be expected to suppress the expression of the above protein by their hybridization with the gene or mRNA coding for the protein. Thus, they can be used as therapeutics for diseases, such as cancer, based on the function the protein is involved in, i.e., telomerase activity.

That is, antisense drugs can be developed from the antisense polynucleotide and its derivatives.

Generally, a method which regulates the expression of a polypeptide by using a polynucleotide containing a base sequence complementary to DNA or mRNA encoding the polypeptide is called the antisense method.

The polynucleotide having a complementary sequence is believed to bind to DNA or mRNA, a bearer of genetic information, somewhere among the following stages, ① transcription from gene to pre-mRNA, ② processing from pre-mRNA to mature mRNA, ③ nuclear membrane passage, and ④ translation to protein, to affect the normal flow of genetic information transduction, thereby regulating the expression of polypeptide.

Generally, a base sequence containing 15 or more bases is considered to be a sequence having specificity (Yokoyama, K., Protein, Nucleic Acid and Enzyme, vol. 38, 754–765, 1994).

Thus, if the antisense polynucleotide and antisense polynucleotide derivative of the invention contain a base sequence complementary to mRNA for the protein and its mutant of the invention, and comprising 15 or more bases, they are speculated to bind specifically to the gene of the invention or mRNA for the gene of the invention.

In incorporating the polynucleotide into a cell, too large a length of the polynucleotide is not suitable.

The antisense polynucleotide or its derivative of the invention may be of any length. However, if it is considered that the antisense polynucleotide of the invention or its derivative is to be taken into a cell to regulate the expression of protein, the antisense polynucleotide or the antisense polynucleotide derivative preferably has a base sequence complementary to mRNA for the gene, the base sequence comprising 15 to 30 bases, preferably 15 to 25 bases, more preferably 18 to 22 bases.

As the antisense polynucleotide or the antisense nucleotide derivative of the invention, various derivatives, i.e., various polynucleotide derivatives having a high power to bind to the desired DNA or mRNA, high tissue selectivity, high cell permeation, high nuclease resistance, and high intracellular stability, can be obtained by publicly known antisense technologies with the aim of enhancing the effect of the polynucleotides as drugs.

In regard to the ease of hybridization, it is generally considered recommendable to design a polynucleotide or a polynucleotide derivative which has a base sequence complementary to the base sequence of a region where a stem loop is formed ("Clinical Immunology, vol. 25", 1200–1206, 1993).

The polynucleotide and its derivative of the invention can, if desired, form a stem loop.

A polynucleotide having a sequence complementary to the sequence near the initiation codon, ribosome binding site, capping site, or splice site can generally be expected to be highly effective in suppressing expression ("Japanese Journal of Cancer and Chemotherapy, vol. 20, No. 13", pp. 1899–1907).

Thus, the polynucleotide or polynucleotide derivative of the invention, which has a sequence complementary to the sequence near the initiation codon, ribosome binding site, capping site, or splice site of the gene encoding the protein or its mutant of the invention, or mRNA for the gene, can be expected to have a high effect of suppressing expression.

Derivatives, which are now generally known, are preferably derivatives with at least one of nuclease resistance, tissue selectivity, cell permeation, and binding force being enhanced. Particularly preferred polynucleotide derivatives are shown to be derivatives having a phosphorothioate bond (see "Japanese Journal of Cancer and Chemotherapy", vol. 20, No. 13, 1899–1907, 1993) as a skeletal structure.

The polynucleotide and its derivatives of the invention also include derivatives having these functions or the above structure.

In connection with a method for producing the antisense polynucleotide derivative of the invention, it is possible to use, for example, the method described in "Antisense Research and Applications" (Michael J. GAIT, pp. 290–299, CRC Publishing, Florida, 1993).

In the case of native DNA or RNA, for example, it can be synthesized by means of a chemical synthesizer, or the antisense polynucleotide of the invention can be obtained by PCR using the gene encoding the protein of the invention as template.

Of the methylphosphonate type or phosphorothioate type derivatives, some can be synthesized by a chemical synthesizer (e.g., Model 394 of Perkin-Elmer Japan).

In this case, the procedure is performed in accordance with an operating guide attached to the chemical synthesizer, and the resulting synthetic product is purified by HPLC using reverse phase chromatography, whereby the desired polynucleotide or polynucleotide derivative can be obtained.

(Application Examples)

As generally explained above, gene therapy and various other applications can be achieved by using the whole or part of the gene of the invention, the protein encoded thereby, and their mutants. Some examples of these applications will be explained in detail below.

(1) Example of Application to Gene Therapy

By expressing the antisense RNA of the invention intracellularly, translation into CRT-1 protein can be inhibited.

For this purpose, the total length of pCRT-1 or part of cDNA is incorporated into a cloning site of an expression vector for a suitable animal cell in the reverse direction, whereby antisense RNA can be prepared with the use of a suitable promotor.

The above material of the invention is also applicable as an intracellular antibody which suppresses the activity of pCRT-1 protein.

Concrete examples are HIV therapy (Marasco W. A., Gene Therapy (1997) 4, 11–15) and breast cancer therapy (Wright M., et al., Gene Therapy (1997) 4, 317–322), as already reported.

The monoclonal antibody against CRT-1 can be isolated by the hybridoma method or the antibody library method.

The monoclonal antibody that can suppress the activity of CRT-1 is selected, and then cDNA encoding the variable region of the antibody can be isolated from hybridoma cells.

The intracellular antibody can be constructed based on the construction of a single-stranded antibody.

That is, variable regions of the H chain and the L chain are joined together by a linker sequence, e.g., a 15-amino acid sequence ((four Gly's and Ser)×3), and the joining product can be expressed intracellularly by a suitable expression vector.

When a mutant of CRT-1 is expressed in a cell as a dominant negative mutant, it can suppress the activity of CRT-1.

The dominant negative mutant is constructed, for example, based on a mutant which binds to a telomere sequence, but which is deficient in DNA synthesizing ability.

The dominant negative mutant shows competitive inhibition of normal CRT-1.

It is also possible to inhibit CRT-1 by introducing into a cell a ribozyme capable of specifically decomposing the mRNA of CRT-1.

A ribozyme is an RNA molecule with the activity of excising RNA sequence-specifically, and is known as a gene therapy of cancer or HIV (Looney D. and Yu M., Methods in Molecular Biology (1997) 74, 469–486; Duarte E. A., et al., Methods in Molecular Biology (1997) 74, 459–468).

(2) Applicability to Identification of an Intracellular Factor Interacting with CRT-1

Studies of telomerase in Tetrahymena and yeast have suggested that telomerase in the cell forms complexes with a plurality of protein factors (Collins K., et al., Cell (1995) 81, 677–686; Linger J., et al., Science (1997) 276, 561–567).

The factors interacting with CRT-1 can be isolated, for example, by the two-hybrid method, a publicly known technique using yeast (Cowell I. G., Method in Molecular Biology (1997) 69, 185–202).

(3) CRT-1 Protein can be Provided as a Research Material, in Crystallized Form, for Structural Analysis, and can also be Used in Drug Designing.

The protein can also be used as a material for reconstitution of an enzyme system having telomerase activity.

Such a reconstitution system is usable in searching for a substance which regulates telomerase activity.

The present invention will now be described with reference to Examples to be offered below. However, the invention is not restricted by these Examples.

EXAMPLE 1 cDNA Cloning (1) Preparation of HL-60 mRNA and Construction of cDNA Library

Total RNA was prepared from HL-60 strain in accordance with the method of Chirgwin et al. (1979) (Biochemistry 18, 5294–5299), and poly A+RNA was prepared with the use of mRNA Purification Kit (Pharmacia) in accordance with the manufacturer's instructions.

HL-60 cDNA libraries for 5'RACE and 3'RACE were constructed with the use of Marathon™ cDNA Amplification Kit (CLONTECH) in accordance with the manufacturer's instructions.

(2) 5'RACE Method

Primers for amplifying the 5' region of a gene having a reverse transcriptase-like motif, i.e., hTRT5 (sequence: 5'-ccgctcgtagttgagcacgctgaa-3') and telo-rev (sequence: 5'-accctcttcaagtgctgtc-3') were designed based on a human-derived EST clone (GenBank Accession Number AA281296) having high homology to a telomerase catalytic subunit of Ciliophora Euplotes or the yeast S. cerevisiae.

These primers were obtained from Sawady Technology (as were the primers to be used below).

Using Takara LA PCRTM Kit Ver. 2 (Takara Shuzo), gene amplification was performed under the following conditions:

A reaction mixture (50 μl) was prepared to have a composition comprising 1×LA PCR Buffer II ($Mg^{2+}$), 0.2 mM dNTP, 0.2 μM of the hTRT5 primer and AP1 primer (attached to Marathon™ cDNA Amplification Kit), 2 μl of the cDNA library for 5'RACE, and 5U Takara LA Taq. The reaction mixture was reacted with the use of GeneAmp PCR System 2400 of Perkin-Elmer/ABI under the following conditions: 94° C. 1 min; 30 cycles of 94° C. 15 sec, 68° C. 3 min, and 68° C. 7 min.

The reaction product was diluted 1:50. With 1 μl of this dilution as template, and using 0.2 μM of the telo-rev primer and AP2 primer (attached to Marathon™ cDNA Amplification Kit), the reaction was performed under the following conditions: 94° C. 1 min; 15 cycles of 94° C. 15 sec, 68° C. 3 min, and 68° C. 7 min.

The composition of the reaction mixture, other than the primers and the template DNA, was the same as that of the former reaction mixture.

The reaction product at the second stage was purified with PCR Purification Kit (QIAGEN), and subcloned into a pGEM-T vector (Promega). The base sequences of the resulting clones were determined using AmpliTaq FS Prism ready reaction cycle sequencing Kit (Perkin-Elmer/ABI).

As a result, a gene having a reverse transcriptase-like motif was identified.

The 3'-terminal 213 bp portion of an isolated sequence had the same sequence as that of hEST2/hTRT1 (Meyerson M. et al., (1997) Cell 90, 785–795; Nakamura T. M. et al., (1997) Science 277, 955–959), which had been isolated earlier as a gene having a reverse transcriptase-like motif, but the portion upstream from the 214 bp portion on the 3'-terminal side had an entirely different structure.

(3) 3'RACE Method

Primers for 3'RACE, i.e., hRT1 (sequence: 5'-tgcgtttcctgccgagtgtgtgttgatcc-3') (SEQ ID NO: 5), hRT3 (sequence: 5'-tgcacagatgaagatgtggagactcacgag-3) (SEQ ID NO: 6), and telo-for (sequence: 5'-agttcctgcactggctgatgagtg-3') (SEQ ID NO: 7), were designed based on the sequences of five fragments obtained by the 5'RACE method.

3'RACE was performed under the following conditions as was 5'RACE:

Using Takara LA PCRTM Kit Ver. 2, gene amplification was performed under the following conditions:

A reaction mixture (50 μl) was prepared to have a composition comprising 1×LA PCR Buffer II ($Mg^{2+}$), 0.2 mM dNTP, 0.2 μM of the hRT1 or hRT3 primer and AP1 primer, 2 μl of the cDNA library for 3'RACE, and 5U Takara LA Taq. The reaction mixture was reacted under the following conditions: 94° C. 1 min; 30 cycles of 94° C. 15 sec, 68° C. 3 min, and 68° C. 7 min.

The reaction product was diluted 1:50. With 1 μl of this dilution as template, and using 0.2 μM of the telo-for primer and AP2 primer, the reaction was performed under the following conditions: 94° C. 1 min; 15 cycles of 94° C. 15 sec, 68° C. 3 min, and 68° C. 7 min.

The composition of the reaction mixture, other than the primers and the template DNA, was the same as that of the initial reaction mixture.

The reaction product at the second stage was purified with PCR Purification Kit, and subcloned into a pGEM-T vector. The base sequences of the resulting clones were determined using AmpliTaq FS Prism ready reaction cycle sequencing Kit.

(4) Acquisition of Gene Having Region Encoding Amino Acids by RT-PCR

From the gene fragments obtained by the 3'RACE method, primer hCRT-rev (sequence: aagatgaagtctcactctgttgcccaggctggagtg-3') (SEQ ID NO: 8) and primer hCRT-rev2 (sequence: 5'-ctgaaaaactcatatattcagtattttactcccacag-3') (SEQ ID NO 13) were designed as primers to be hybridized with the 3'-terminal of cDNA. Using these primers and hRT3, and with the cDNA library for RACE as a template, a gene comprising a region encoding amino acids was obtained.

The reaction conditions were as follows:

A reaction mixture (50 µl) was prepared to comprise 1×LA PCR Buffer II ($Mg^{3}$+), 0.2 mM dNTP, 0.2 µM of the hCRT-rev primer (or hCRT-rev2 primer) and hRT3 primer, 2 µl of the cDNA library for RACE, and 5U Takara LA Taq. The reaction mixture was reacted with the use of GeneAmp PCR System 2400 of Perkin-Elmer/ABI under the following conditions: 94° C. 1 min; 30 cycles of 94° C. 15 sec, 68° C. 3 min, and 68° C. 7 min.

The resulting reaction product was subcloned into a PGEM-T vector, and the base sequences of the resulting clones were determined using AmpliTaq FS Prism ready reaction cycle sequencing Kit (Perkin-Elmer/ABI).

Several types of splicing variants were obtained, and sequences having possible reading frames for reverse transcriptase-like proteins were speculated from them.

When the primer hCRT-rev was used, two types of the above base sequences were obtained.

One of the base sequences, and an amino acid sequence deduced therefrom are shown in SEQ ID NO: 1 and SEQ ID NO: 2 in the Sequence Listing.

The other base sequence, and an amino acid sequence deduced therefrom are shown in SEQ ID NO: 9 and SEQ ID NO: 10 in the Sequence Listing.

The base sequence obtained through the use of the primer hCRT-rev2, and an amino acid sequence deduced therefrom are shown in SEQ ID NO: 11 and SEQ ID NO: 12 in the Sequence Listing.

The amino acid sequence of SEQ ID NO: 10 was the amino acid sequence of SEQ ID NO: 2 having Leu inserted at the 361st position.

The amino acid sequence of SEQ ID NO: 12 was the amino acid sequence of SEQ ID NO: 2 in which Leu had been inserted at the 361st position, Arg at the 437th position had been substituted by Ser, and amino acid residues had been further added.

EXAMPLE 2

Genetic Diagnosis by RT-PCR Method

1. Analysis of Expression Distribution

Using primers (hRT3 and hTRT5) which amplify the gene CRT-1 having a reverse transcriptase-motif according to the invention, the expression of hCRT in cancer cell strains and testis having telomerase activity, and a normal diploid cell strain WI-38 having no telomerase activity was investigated by RT-PCR.

RT-PCR was performed by the following procedure:

Total RNA was prepared from various cultured cells in accordance with the guanidine isothianate/phenol method (Chomc zynski and Sacchi (1987) Anal. Biochem. 162, 156–159), and cDNA was synthesized with the use of First-Strand cDNA Synthesis Kit (Pharmacia) in accordance with the attached instruction manual.

Using 1/50 of the reaction product as template, PCR was performed under the following conditions:

The reaction was to be carried out on a 20 µl scale, and a reaction mixture was prepared to comprise 10 mM Tris-HCl, pH 8.3, 50 mM KCl, 1.5 mM $MgCl_2$, 0.2 µM of primers hRT3 and hTRT5, and 1U AmpliTaqGold (Perkin-Elmer).

Using GeneAmpPCR System 9600 of Perkin-Elmer/ABI, the reaction was performed under the conditions: 94° C. 10 min; 40 cycles of 94° C. 30 sec, 55° C. 30 sec, and 72° C. 1 min.

The reaction product was analyzed by 1% agarose electrophoresis.

The expression of hCRT gene was observed in the cancer cell strains and the testis, showing the expression of this gene to be correlated with telomerase activity.

As positive controls for the reverse transcription reaction, the results of RT-PCR of G3PDH (glycer aldehyde 3-phosphate dehydrogenase) gene are shown in FIG. 1.

INDUSTRIAL APPLICABILITY

The present invention isolates a novel gene having a reverse transcriptase motif, and provides its whole base sequence determined. The invention also provides a protein encoded by the gene, and an antibody against the protein.

Such base sequence information, protein and antibody can be used effectively in developing a method for detecting telomerase activity, a method for detecting a cancer cell, a telomerase activity inhibitor, and a method for screening a telomerase activity inhibitor.

What is claimed is:

1. An isolated protein comprising the amino acid sequence of SEQ ID NO: 2.

2. An isolated protein comprising an amino acid sequence containing one amino acid substitution, deletion or addition as compared to SEQ ID NO: 2 wherein said protein has reverse transcriptase activity.

3. An isolated protein comprising the amino acid sequence of SEQ ID NO: 10.

4. An isolated protein comprising an amino acid sequence containing one amino acid substitution, deletion or addition as compared to SEQ ID NO: 10 wherein said protein has reverse transcriptase activity.

5. An isolated protein comprising the amino acid sequence of SEQ ID NO: 12.

6. An isolated protein comprising an amino acid sequence containing one amino acid substitution, deletion or addition as compared to SEQ ID NO: 12 wherein said protein has reverse transcriptase activity.

* * * * *